United States Patent [19]

Kishi et al.

[11] Patent Number: 5,140,044

[45] Date of Patent: Aug. 18, 1992

[54] UCN-1028D DERIVATIVES

[75] Inventors: Teruo Kishi, Tama; Hiromitsu Saito, Sagamihara; Hiroshi Sano, Machida; Isami Takahashi, Tama; Tatsuya Tamaoki, Machida, all of Japan

[73] Assignee: Kyowa Hakko Kogyo Co., Ltd., Tokyo, Japan

[21] Appl. No.: 500,245

[22] Filed: Mar. 27, 1990

[30] Foreign Application Priority Data

Mar. 31, 1989 [JP] Japan .................................. 1-81200

[51] Int. Cl.$^5$ ............... A01N 35/00; A01N 47/10; A01N 37/00; C07C 50/10; C07C 303/00; C07C 261/00; C07C 49/115
[52] U.S. Cl. ............................ 514/480; 514/481; 514/483; 514/510; 514/513; 514/517; 514/533; 514/541; 514/542; 514/544; 514/546; 514/548; 514/550; 514/551; 514/680; 514/686; 552/295; 558/44; 558/46; 558/47; 558/48; 558/49; 558/50; 558/51; 558/52; 558/260; 558/266; 558/267; 558/268; 558/269; 558/276; 558/277; 558/392; 558/398; 558/406; 558/408; 558/409; 558/410; 558/427; 560/9; 560/20; 560/22; 560/23; 560/76; 560/28; 560/29; 560/32; 560/33; 560/187; 560/188; 560/189; 568/306; 568/326
[58] Field of Search ............... 552/284, 295; 558/46, 558/47, 49, 50, 52, 55, 230, 48, 51; 560/32, 33, 85, 12, 363, 28, 26, 29, 9, 20, 22, 23, 187, 188, 189; 568/347, 351, 352, 326; 514/680, 480, 510, 541, 481, 483, 513, 533, 542, 544, 548, 550, 551, 686

[56] References Cited

U.S. PATENT DOCUMENTS 4,719,236 1/1988 Bair ........................................ 568/705
4,731,468 3/1988 Gessou et al. ...................... 568/326
4,945,108 7/1990 Grabley et al. ..................... 568/326

OTHER PUBLICATIONS

The Journal of Antibiotics, vol. XLII, No. 10, 1470–1474, 1475–1481.
Agricultural & Biological Chemistry, 39, (8), 1683–1684 (1975).
J. Jap. Pasture, 28, (4), 426–432 (1983).
Phytochemistry, 27 (6), 1675–1678 (1988).

*Primary Examiner*—C. Warren Ivy
*Assistant Examiner*—Raymond Covington
*Attorney, Agent, or Firm*—Antonelli, Terry, Stout & Kraus

[57] ABSTRACT

A UCN-1028D derivative represented by the formula:

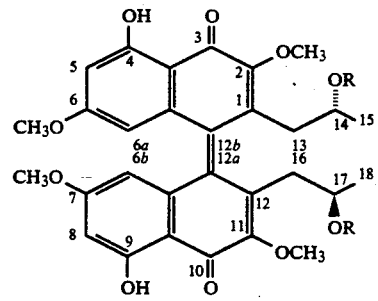

has protein kinase C inhibitory activity and is expected to be used as an active ingredient in anti-tumor agents, etc.

9 Claims, No Drawings

UCN-1028D DERIVATIVES

BACKGROUND OF THE INVENTION

The present invention relates to UCN-1028D derivatives having protein kinase C inhibitory activity and anti-tumor activity and which are useful as anti-tumor agents.

As a substance having perylenequinone skeleton and which is structurally related to the compounds of the present invention, there is known Phleichrome isolated as a plant poison from *Cladosporium phlei* which causes spots on pasture [Agricultural & Biological Chemistry, 39, 1683 (1975), J. Jap. Pasture, 28 (4), 426 (1983)]. Similar substances UCN-1028A and UCN-1028C having anti-tumor and protein kinase C inhibitory activity are disclosed in European Patent Publication No. 0284358.

The structural formulae of UCN-1028A and UCN-1028C are shown below.

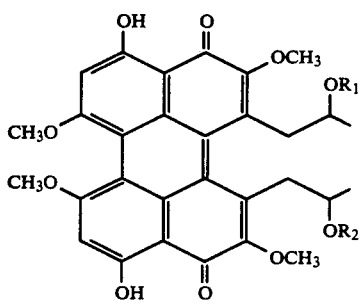

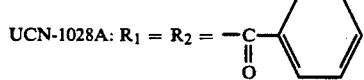

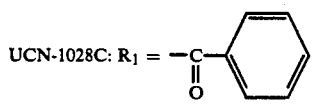

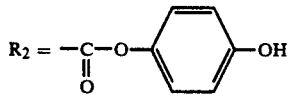

SUMMARY OF THE INVENTION

The present invention provides UCN-1028D derivatives [hereinafter referred to as Compounds (I)] represented by general formula (I):

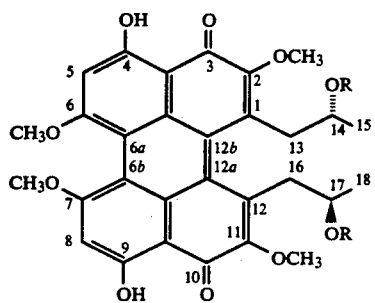

wherein R represents hydrogen,
(a)

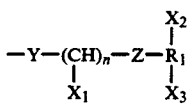

wherein Y represents

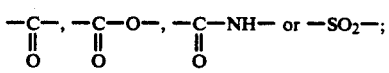

n represents an integer of 0 to 4; Z represents O, NH or a single bond; $R_1$ represents an aryl group or a heterocyclic group; $X_1$ represents hydrogen, $OR_2$ (wherein $R_2$ represents hydrogen, a straight-chain or branched alkyl group having 1 to 5 carbon atoms, or a straight-chain or branched alkanoyl group having 1 to 5 carbon atoms), $NR_3R_4$ (wherein $R_3$ and $R_4$ independently refer to $R_2$, and $R_2$ has the same significance as defined above), $NO_2$, $SR_2$ (wherein $R_2$ has the same significance as defined above) CN or $CO_2R_5$ (wherein $R_5$ represents hydrogen or an alkyl group having 1 to 5 carbon atoms), and when n is 2 or more, $X_1$ may be the same or different from each other; $X_2$ and $X_3$ each represents a substituent on $R_1$ and independently represent $X_1$ (wherein $X_1$ has the same significance as defined above) or a straight-chain or branched alkyl group having 1 to 5 carbon atoms; with the proviso that when n is 0, Z represents a single bond, and when n is 0, Y is

and $R_1$ is phenyl, the perylenequinone ring takes R configuration with respect to the bond between 6a and 6b, or (b)

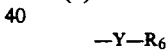

wherein Y has the same significance as defined above; and $R_6$ represents a straight-chain or branched alkyl group having 1 to 12 carbon atoms, a cyclic alkyl group having 3 to 8 carbon atoms, a straight-chain or branched alkenyl group having 2 to 6 carbon atoms and which contains 1 to 3 double bonds, or a group obtained by substituting at least one hydrogen of these groups with $X_4$ (wherein $X_4$ refers to $X_1$ excluding hydrogen, and $X_1$ has the same significance as defined above).

Compounds (I) have protein kinase C inhibitory activity and are expected to be useful as active ingredients in anti-tumor agents, etc.

DETAILED DESCRIPTION OF THE INVENTION

In the definitions of the groups in general formula (I), examples of the aryl group include phenyl and naphthyl, and examples of the heterocyclic group include aromatic heterocyclic groups such as pyridyl, pyrimidinyl, pyrazinyl, furyl, pyrrolyl and imidazolyl and alicyclic heterocyclic groups such as pyrrolidinyl and piperidinyl. Examples of the straight-chain or branched alkyl group having 1 to 5 carbon atoms include methyl, ethyl, n-propyl, isopropyl, n-butyl, isobutyl, sec-butyl, tert-butyl, n-pentyl and neopentyl. Examples of the straight-chain or branched alkyl group having 1 to 12 carbon atoms include, in addition to the alkyl groups mentioned above, hexyl, heptyl, octyl, nonyl, decyl, undecyl and dodecyl. Examples of the straight-chain or branched alkanoyl group having 1 to 5 carbon atoms include formyl, acetyl, propionyl, butyryl and valeryl. Examples of the cyclic alkyl group having 3 to 8 carbon atoms include cyclopropyl, cyclopentyl, cyclohexyl, cycloheptyl and cyclooctyl. Examples of the straight-chain or branched alkenyl group having 2 to 6 carbon atoms and which contains 1 to 3 double bonds include vinyl, allyl, propenyl, butenyl and hexenyl.

In the perylenequinone derivatives having bulky substituents at the 1- and 12-positions and at the 6- and 7-positions, the perylenequinone skeleton does not take a plane structure because of restricted rotation due to these substituents, but twists on its axis of the bonds between the 6a- and 6b-positions and the 12a- and 12b-positions. Thus, isomers are present with the perylenequinone ring.

That is, UCN-1028D having the following structural formula:

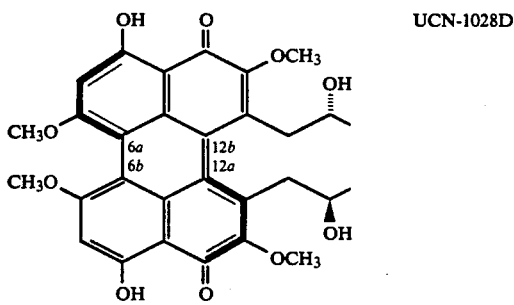

UCN-1028D in which the perylenequinone ring takes S configuration on the bond between the 6a- and 6b-positions is isomerized by heating in a toluene or xylene solution to form an isomer of UCN-1028D (hereinafter referred to as UCN-1028 iso-D) represented by the following structural formula:

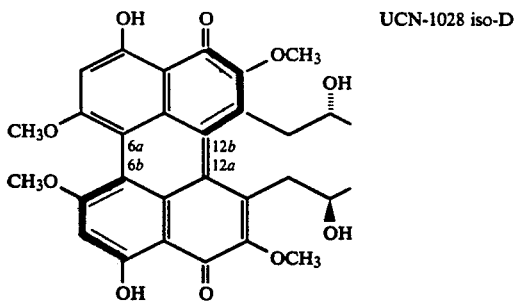

UCN-1028 iso-D in which the perylenequinone ring takes R configuration on the bond between the 6a- and 6b-positions. These compounds reach the equilibrium in 1 : 1.

UCN-1028D and UCN-1028 iso-D can be separated from each other by thin layer chromatography or column chromatography using silica gel. UCN-1028 iso-D can be thermally isomerized into UCN-1028D under the same conditions as in the isomerization of UCN-1028D.

The present invention includes UCN-1028D and derivatives thereof, UCN-1028 iso-D and derivatives thereof, and a mixture thereof.

Compounds (I) other than UCN-1028 iso-D can be produced by the following steps.

UCN-1028D can be obtained by alkaline hydrolysis of UCN-1028A or UCN-1028C.

The hydrolysis of UCN-1028A or UCN-1028C efficiently proceeds by treating UCN-1028A or UCN-1028C with an aqueous solution of an inorganic base such as sodium hydroxide, potassium hydroxide, barium hydroxide, sodium carbonate or potassium carbonate in a solvent miscible with water such as methanol, ethanol, acetone or dimethylsulfoxide at 0° C. to 100° C.

Compounds (I-1) [Compounds (I) wherein Y is

Compounds (I-2) [Compounds (I) wherein Y is

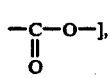

Compounds (I-3) [Compounds (I) wherein Y is $-SO_2-$] and Compounds (I-4) [Compounds (I) wherein Y is

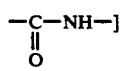

can be prepared by Processes 1, 2, 3 and 4, respectively.

PROCESS 1

Compounds (I-1) can be prepared by allowing UCN-1028D or UCN-1028 iso-D to react with at least 2 equivalents of a reactive derivative of carboxylic acid, for example, an acid anhydride or an acid halide such as acid chloride or acid bromide at $-20°$ to 100° C. in an organic solvent in the presence of a base. As the organic solvent, chloroform, dichloromethane, dichloroethane, pyridine, etc. may be used singly or in combination. As the base, pyridine, 4-dimethylaminopyridine, 4-pyrrolidinopyridine, triethylamine, etc. may be used singly or in combination. When pyridine is used as the base, it is unnecessary to use any additional organic solvent. It is preferred that the base be used in an equimolar amount or more based on the reactive derivative of carboxylic acid.

Compounds (I-1) may also be prepared by allowing UCN-1028D or UCN-1028 iso-D to react with at least 2 equivalents of carboxylic acid and a condensing agent at $-20°$ to 100° C. in an organic solvent in the presence of a base. The same organic solvents and the bases as mentioned above can be used in this method. As the condensing agent, N,N'-dicyclohexylcarbodiimide, N,N'-diisopropylcarbodiimide, 1-cyclohexyl-3-(2-morpholinoethyl)carbodiimide, 1-ethyl-3-(3-dimethylaminopropyl)carbodiimide, etc. may be used. When pyridine is used as the base, pyridine is preferably used in an equimolar amount or more based on the carboxylic acid. In the case of bases other than pyridine, it is preferred to use at least 0.05 equivalent of a base based on the carboxylic acid.

In cases where the carboxylic acid used in the two methods for preparing Compounds (I-1) described above is substituted with an amino group, a monoalkylamino group, a carboxyl group, a hydroxyl group, a thiol group or the like, these functional groups are protected with appropriate protective groups prior to the reaction and if necessary, the protective groups are removed after the reaction. As the protective group, those which are capable of being removed under weakly alkaline or acidic conditions are preferred. Details of these protective groups and the conditions for introducing and removing the same are described in Green, *Protective Groups in Organic Synthesis*, John Wiley & Sons Incorporated, 1981.

For example, when the functional group is the amino group, p-methoxybenzyloxycarbonyl group, t-butyloxycarbonyl group and t-amyloxycarbonyl group are appropriate as the protective group. Removal of the protective group can be effected by treating Compound (I-1) with at least 2 equivalents of trifluoroacetic acid at −20° to 50° C. in a halogen-type organic solvent or in the absence of a solvent. Examples of the halogen-type organic solvent are chloroform, dichloromethane and dichloroethane.

When the functional group is the carboxyl group, a method wherein t-butyl group, p-methoxybenzyl group, 2,4,6-trimethylbenzyl group, pentamethylbenzyl group, benzhydryl group or methylthiomethyl group is used as the protective group and the protective group is removed in a similar manner as in the removal of an amino-protecting group; a method wherein t-butyl group, p-methoxybenzyl group, tetrahydropyranyl group or tetrahydrofuranyl group is used as the protective group and the protective group is removed by the treatment with acetic acid or formic acid in aqueous tetrahydrofuran or hydrated dioxane; and the like are applicable. Further, when the functional group is the carboxyl group, an intramolecular acid anhydride may be formed from the carboxyl group and another carboxyl group which is to be used for esterification.

When the functional group is the hydroxyl group, tetrahydropyranyl group, 4-methoxytetrahydropyran-4-yl group, tetrahydrofuranyl group, triphenylmethyl group, methoxymethyl group, 1-ethoxyethyl group, 1-methyl-1-methoxyethyl group, t-butyl group, trimethylsilyl group, t-butyldimethylsilyl group, t-butyldiphenylsilyl group, triphenylsilyl group, etc. are appropriate as the protective group. The protective group can be removed by the treatment with an acid in the absence of a solvent or in an organic solvent miscible with water or in a mixture of such a solvent and water. Examples of the organic solvent miscible with water include methanol, ethanol, tetrahydrofuran and dioxane. Examples of the acid include formic acid, acetic acid, trifluoroacetic acid, p-toluenesulfonic acid, pyridinium p-toluenesulfonate, ion exchange resin of the sulfonic acid type, hydrochloric acid and sulfuric acid. It is also possible to use formyl group or trifluoroacetyl group as the protective group. In this case, the protective group can be removed by the treatment with ammonia or an inorganic alkali in an organic solvent miscible with water or in a solvent mixture of the organic solvent and water. The same organic solvents miscible with water as mentioned above can be used in such a case. As the inorganic alkali, potassium hydrogencarbonate, sodium hydrogencarbonate, potassium carbonate and sodium carbonate may be mentioned. In cases where the hydroxyl group is present on the aromatic ring of the aryl or aralkyl, this phenolic hydroxyl group is protected using acetyl group as the protective group followed by condensation with UCN-1028D or UCN-1028 iso-D in a similar manner as described above. The protective group can be removed by the treatment with ammonia or an inorganic alkali in an organic solvent miscible with water or in a mixture of such a solvent and water. As the organic solvent miscible with water and the inorganic alkali, those which are mentioned above can be used.

When the functional group is the thiol group, p-methoxybenzyl group, diphenylmethyl group, triphenylmethyl group, acetyl group, benzoyl group, etc. may be used as the protective group and removal of the protective group can be effected by the treatment with trifluoroacetic acid. Further, when acetyl group or benzoyl group is used as the protective group, the protective group may also be removed by the treatment with ammonia or an inorganic alkali in an organic solvent miscible with water or in a mixture of such a solvent and water. As the organic solvent miscible with water and the inorganic alkali, those which are mentioned above can be used.

PROCESS 2

Compounds (I-2) [Compounds (I) wherein Y is

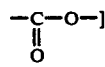

can be prepared by allowing UCN-1028D or UCN-1028 iso-D to react with at least 2 equivalents of a halogenated carbonic acid ester such as a halogenated alkyl formate, a halogenated aralkyl formate or a halogenated aryl formate at −20° to 50° C. in an organic solvent in the presence of a base. As the organic solvent and the base, those which are mentioned above can be used singly or in combination. Where pyridine is used as the base, it may be unnecessary to use any organic solvent. It is preferred that the base be used in an equimolar amount or more based on the halogenated formic acid ester.

PROCESS 3

Compounds (I-3) [Compounds (I) wherein Y is —SO$_2$-] can be prepared by allowing UCN-1028D or UCN-1028 iso-D to react with at least 2 equivalents of a sulfonic acid halide such as an alkylsulfonyl halide, an aralkylsulfonyl halide or an arylsulfonyl halide at −20° to 50° C. in an organic solvent in the presence of a base. As the organic solvent and the base, those which are mentioned above can be used singly or in combination. When pyridine is used as the base, it may be unnecessary to use any organic solvent. It is preferred that the base be used in an equimolar amount or more based on the sulfonic acid halide.

PROCESS 4

Compounds (I-4) [Compounds (I) wherein Y is —CONH—] can be prepared by allowing UCN-1028D or UCN-1028 iso-D to react with at least 2 equivalents of an alkyl isocyanate, an aralkyl isocyanate or an aryl isocyanate at 0° to 100° C. in an organic solvent. As the organic solvent, those which are mentioned above, as well as benzene and toluene, can be used singly or in combination.

The intermediates and the desired compounds in the processes described above can be isolated and purified by purification methods conventionally used in organic synthetic chemistry, for example, by filtration, extraction, washing, drying, concentration, recrystallization and various kinds of chromatography. The intermediates may be used in the subsequent reaction without any particular purification.

Compounds (I) sometimes exist in the form of an adduct of water or various solvents. Such adducts are also included in the present invention.

Representative examples of Compounds (I) are shown in Table 1.

TABLE 1

Compound (I): structure with perylenequinone ring bearing OH, OCH$_3$, OR substituents.

| Compound No. | R |
|---|---|
| 1 | acetyl |
| 2 | butyryl |
| 3 | hexanoyl |
| 4 | heptanoyl |
| 5 | decanoyl |
| 6 | dodecanoyl |
| 7 | 4-pentenoyl |
| 8 | cyclohexanecarbonyl |
| 9 | phenylacetyl |
| 10 | 3-phenylpropionyl |
| 11 | 4-phenylbutyryl |
| 12 | 1-naphthylacetyl |
| 13 | phenyloxyacetyl |
| 14 | L-leucyl |
| 15 | L-isoleucyl |
| 16 | D-phenylglycyl |
| 17 | L-phenylalanyl |
| 18 | D-phenylalanyl |
| 19 | N-methyl-L-phenylalanyl |
| 20 | L-prolyl |
| 21 | 6-aminohexanoyl |
| 22 | succinyl |
| 23 | 5-acetylthiopentanoyl |
| 24 | p-acetoxybenzoyl |
| 25 | p-cyanobenzoyl |
| 26 | p-hydroxybenzoyl |
| 27 | p-methoxybenzoyl |
| 28 | p-methoxycarbonylbenzoyl |
| 29 | p-methylbenzoyl |
| 30 | p-nitrobenzoyl |
| 31 | 1-naphthoyl |
| 32 | 2-naphthoyl |
| 33 | isonicotinyl |
| 34 | pyrazine-2-carbonyl |
| 35 | 2-furoyl |
| 36 | methoxycarbonyl |
| 37 | benzyloxycarbonyl |
| 38 | phenyloxycarbonyl |
| 39 | methanesulfonyl |
| 40 | toluenesulfonyl |
| 41 | propylaminocarbonyl |
| 42 | phenylaminocarbonyl |
| 43 | hydrogen (UCN-1028 iso-D) |
| 44 | benzoyl |
| 45 | hydrogen (UCN-1028D) |

Note)
The perylenequinone ring in the above structural formula of Compounds (I) takes S configuration on the bond between the 6a- and 6b-positions in Compound Nos. 1 through 42 and 45, and takes R configuration in Compound Nos. 43 and 44.

The protein kinase C. inhibitory activity and anti-tumor activity of Compounds (I) are explained below by referring to experimental examples.

EXPERIMENTAL EXAMPLE 1

Protein kinase C inhibitory activity

The protein kinase C inhibitory activity was measured by the method of Kikkawa, et al. [Journal of Biological Chemistry, 257, 13341 (1982)].

That is, 10 μl of a test solution containing a UCN-1028D derivative was added to 250 μl of a solution containing 2.5 μmoles of magnesium acetate, 50 μg of Histone Type II S (manufactured by Sigma Co., Ltd.), 20 μg of phosphatidyl serine, 0.8 μg of diolein, 25 nmoles of $CaCl_2$, 5 μg of crude enzyme (partially purified from rat brain according to the method of Kikkawa, et al.) and 5 μmoles of Tris-hydrochloride buffer (pH 7.5), followed by incubation at 30° C. for 3 minutes. Then, phosphorylation was initiated by addition of 1.25 nmoles of [γ-$^{32}$P]ATP (5 to $10 \times 10^3$ cpm/nmole), followed by incubation at 30° C. for 3 minutes The reaction was stopped by adding 25% trichloroacetic acid (TCA), and the reaction solution was filtered through a cellulose acetate membrane (pore size: 0.45 μm) (manufactured by Toyo Filter Paper Co., Ltd.). After the membrane was washed four times with 5% TCA, radioactivity remaining on the membrane was measured. As a control, the same procedure as above was repeated without addition of the test solution and radioactivity was likewise measured. The concentration of the test solution showing 50% inhibition as compared with the control was expressed as $IC_{50}$.

The results are shown in Table 2.

EXPERIMENTAL EXAMPLE 2

Anti-tumor activity

The anti-tumor activity was determined using BALB 3T3 cells transformed with the carcinogenic gene H-ras (hereafter referred to as BALB 3T3/H-ras).

BALB 3T3/H-ras cells were suspended in a medium comprising DME medium (manufactured by Nissui Pharmaceutical Co., Ltd.) and 10% fetal calf serum (hereafter referred to as medium A) to a concentration of $3.0 \times 10^4$/cells ml. The cell suspension thus prepared was put into wells of a 96-well microtiter plate in an amount of 0.1 ml per well. After culturing at 37° C. for 20 hours in a $CO_2$-incubator, 0.1 ml each of a test solution appropriately diluted with medium A was added to each well. The cells were further cultured at 37° C. for 72 hours in the $CO_2$-incubator and the culture supernatant was removed. After being washed once with physiological saline, the residue was treated with 0.1 ml of methanol for 10 minutes to fix the cells. Thereafter, the cells were stained with 0.1 ml of Giemsa staining solution [Giemsa staining stock solution (Merck Art 9204; manufactured by Merck Inc.) : physiological saline=1 : 10] for 5 minutes. After the staining solution was removed, the residue was washed once with 0.2 ml of water. The pigment was extracted with 0.2 ml of 0.1 N hydrochloric acid and the absorbance at 620 nm was measured with a microplate reader. By comparing the absorbance of untreated cells with those of the cells treated with the test compound at known concentrations, the concentration of the test compound at which the growth of the cells is inhibited by 50% ($IC_{50}$) was calculated.

The results are shown in Table 2.

TABLE 2

| Compound No. | IC$_{50}$ (μg/ml) | |
|---|---|---|
| | Protein Kinase C Inhibitory Activity | BALB 3T3/H-ras Inhibitory Activity |
| 1 | 1.6 | 0.048 |
| 2 | 0.14 | 0.023 |
| 3 | 0.035 | 0.12 |
| 4 | 0.03 | 0.52 |
| 5 | 0.068 | 7.0 |
| 6 | 0.15 | 4.8 |
| 7 | 0.06 | 0.17 |
| 8 | 0.017 | 0.56 |
| 9 | 0.054 | 0.11 |
| 10 | 0.045 | 0.95 |
| 11 | 0.035 | 2.6 |
| 12 | 0.05 | 1.3 |
| 13 | 0.08 | 0.030 |
| 14 | 0.21 | 0.45 |
| 15 | 0.15 | 0.28 |
| 16 | 0.17 | 0.72 |
| 17 | 0.088 | 0.35 |
| 18 | 0.16 | 0.84 |
| 19 | 0.1 | 0.35 |
| 20 | 0.33 | 3.2 |
| 21 | 0.08 | 2.5 |
| 24 | 0.082 | 0.048 |
| 25 | 0.05 | 0.042 |
| 26 | 0.084 | 0.13 |
| 27 | 0.05 | 0.026 |
| 28 | 0.084 | 0.068 |
| 29 | 0.06 | 0.022 |
| 30 | 0.11 | 0.07 |
| 31 | 0.19 | 1.5 |
| 32 | 0.1 | 1.2 |
| 33 | 0.15 | 0.038 |
| 35 | 0.11 | 0.12 |
| 36 | 0.29 | 0.13 |
| 37 | 0.052 | 0.040 |
| 38 | 0.058 | 0.015 |
| 39 | 0.5 | 0.35 |
| 40 | 0.066 | 0.040 |
| 41 | 0.94 | 0.68 |
| 42 | 0.021 | 0.075 |
| 43 | 0.74 | 1.0 |
| 44 | 0.025 | 0.52 |
| 45 | 3.5 | 2.2 |

UCN-1028D derivatives may be used as anti-tumor agents singly or together with pharmaceutically acceptable carriers. For example, a UCN-1028D derivative is dissolved in a physiological saline solution or in an aqueous solution of glucose, lactose, mannitol, etc. to prepare a suitable pharmaceutical composition for injection. Alternatively, a UCN-1028D derivative or a salt thereof is freeze-dried or mixed with sodium chloride to prepare a powdery injection. The pharmaceutical composition may contain additives well known in the art of medical preparation, for example, pharmaceutically acceptable salts, if necessary. Although the amount of the compound for dosage varies depending upon the age, condition, etc. of the patient, it is suitable to administer the compound in an amount of 0.01 to 20 mg/kg/day for mammals including human beings. Administration may be made once a day (single administration or consecutive administration) or intermittently 1 to 3 times a week or once every 2 to 3 weeks, intravenously. Oral administration is also possible in a similar dose and in a similar manner. Preparations for oral administration include tablets, capsules, powders, granules, ampoules, etc. These preparations contain pharmaceutical auxiliaries well known in the art of medical preparation. Further, intraarterial administration, intraperitoneal administration, intrathoracic administration, etc. are also possible in a similar dose and in a similar manner.

The anti-tumor compositions of the present invention are expected to be effective against leukemia, gastric cancer, colon cancer, lung cancer, breast cancer, uterine cancer, etc. in mammals including human beings.

Certain specific embodiments of the present invention are illustrated by the following examples.

EXAMPLE 1

Preparation of UCN-1028D (Compound 45)

In 300 ml of dimethylsulfoxide was dissolved 8.0 g of UCN-1028A, and 75 ml of 6 N aqueous solution of sodium hydroxide was added to the solution. The mixture was stirred at room temperature overnight. After concentrated hydrochloric acid was added to the mixture to adjust the pH to 6.0, the mixture was extracted with ethyl acetate. The solvent was distilled off and the residue was subjected to chromatography using a column packed with 2 l of HP-20SS (manufactured by Mitsubishi Kasei Corporation) and using 90% methanol as a developing solvent. The fractions containing UCN-1028D were concentrated to dryness. By adding hexane, the residue was powdered to give 4.0 g of UCN-1028D.

Melting point: 230° C. or above.

UV $\lambda_{Max}^{CH3OH}$ (nm): 258(sh), 270, 338, 476, 540(sh), 586.

IR (KBr) $\lambda$max(cm$^{-1}$): 3370, 2960, 2930, 2830, 1600, 1540, 1455, 1420, 1275, 1215, 1155, 1120, 1110, 1080, 995, 965, 920, 835.

$^1$H-NMR [100MHz, CDCl$_3$-CD$_3$OD(10:1)]$\delta$(ppm): 5.86(2H, s), 4.28(6H, s), 4.00-3.50(2H, br), 3.68(6H, s), 3.60 (2H, dd, J=5, 13Hz), 3.00(2H, dd, J=8, 13Hz), 1.04(6H, d, J=7Hz).

EXAMPLE 2

Preparation of 14,17-di-O-acetyl UCN-1028D (Compound 1)

In 2.0 ml of dichloromethane was dissolved 48.4 mg of UCN-1028D, and 0.2 ml of pyridine was added to the solution. With stirring under ice cooling, 25 μl of acetic anhydride was added to the mixture three times at 30-minute intervals. The mixture was stirred for further 30 minutes and then allowed to stand at room temperature for 6.5 hours. One drop of water was added to the reaction mixture, followed by stirring for 10 minutes. Then, 30 ml of ethyl acetate was added to the mixture. The organic layer was washed successively with 15 ml each of water (three times), 1 M hydrochloric acid, water, saturated aqueous solution of sodium hydrogencarbonate and water (twice), dried over anhydrous sodium sulfate and concentrated under reduced pressure. The residue was dissolved in a small quantity of dichloromethane and the solution was loaded on a silica gel thin layer chromatography plate having a thickness of 0.5 mm (20 cm×20 cm) and developed with chloroform-methanol (100 : 2). The part of the silica gel on which a band of the main product was formed was scraped out and extracted with ethyl acetate. The extract was concentrated to give 40.0 mg (72%) of Compound 1.

Melting point: 240° C. or above.

IR (KBr) $\nu$max(cm$^{-1}$): 3100, 2980, 2950, 2870, 2850, 1735, 1605, 1570, 1540, 1460, 1440, 1370, 1335, 1270, 1240, 1210, 1160, 1125, 1105, 1075, 1050, 1035, 995, 965, 950, 920, 840, 780, 760, 725, 680, 660.

$^1$H-NMR (100MHz, CDCl$_3$) $\delta$(ppm): 14.31(2H, s), 6.61(2H, s), 4.50-4.90(2H, m), 4.25(6H, s), 4.04(6H, s), 3.52(2H, dd, J=3, 13Hz), 2.95(2H, dd, J=10, 13Hz), 1.05(6H, d, J=7Hz), 0.76(6H, s).

EXAMPLE 3

Preparation of 14,17-di-O-butyryl UCN-1028D (Compound 2)

UCN-1028D (54.8 mg) was allowed to react with 97 μl of butyric anhydride in 1.5 ml of dichloromethane and 0.2 ml of pyridine at room temperature for 15 hours. The reaction mixture was treated and then subjected to silica gel thin layer chromatography in a similar manner as in Example 2 to give 44.0 mg (64%) of Compound 2.

Melting point: 197°–200° C.

IR (KBr) νmax(cm$^{-1}$): 2970, 2940, 2870, 1725, 1605, 1525, 1455, 1420, 1405, 1380, 1340, 1270, 1240, 1210, 1180, 1155, 1120, 1105, 1075, 1050, 1040, 985, 960, 905, 835, 780, 760, 725, 695, 675, 650.

$^1$H-NMR (100MHz, CDCl$_3$) δ(ppm): 14.46(2H, s), 6.62(2H, s), 4.60–5.00(2H, m), 4.28(6H, s), 4.05(6H, s), 3.50(2H, dd, J=3, 13Hz), 2.93(2H, dd, J=10, 13Hz), 1.13(6H, d, J=7Hz), 0.20–1.40(14H, m).

EXAMPLE 4

Preparation of 14,17-di-O-hexanoyl UCN-1028D (Compound 3)

UCN-1028D (34.6 mg) was subjected to reaction with caproic anhydride in 1.5 ml of dichloromethane and 0.4 ml of pyridine with stirring at room temperature for 48 hours. The reaction was carried out by addition of caproic anhydride in amounts of 86 μl at the start, 43 μl 10 hours after and 29 μl 24 hours after the start of reaction. The reaction mixture was treated and then subjected to silica gel thin layer chromatography in a similar manner as in Example 2 to give 28.5 mg (61%) of Compound 3.

Melting point: 147°–150° C.

IR (KBr) νmax(cm$^{-1}$): 2930, 2860, 1720, 1605, 1520, 1460, 1450, 1420, 1380, 1335, 1275, 1240, 1210, 1160, 1120, 1100, 1080, 1050, 990, 960, 910, 830, 780, 760, 725, 680, 650.

$^1$H-NMR (100MHz, CDCl$_3$) δ (ppm): 14.40(2H, s), 6.59(2H, s), 4.60–5.00(2H, m), 4.24(6H, s), 4.02(6H, s), 3.53(2H, dd, J=3, 13Hz), 2.96(2H, dd, J=10, 13Hz), 1.13(6H, d, J=7Hz), 0.50–1.40(22H, m).

EXAMPLE 5

Preparation of 14,17-di-O-heptanoyl UCN-1028D (Compound 4)

UCN-1028D (40.6 mg) was allowed to react with 35 μl of heptanoyl chloride in 1.5 ml of dichloromethane and 0.2 ml of pyridine with stirring at room temperature for 2 hours. To the mixture was added 35 μl of heptanoyl chloride, and after 30 minutes, 20 μl of heptanoyl chloride was further added. Then, the reaction was continued for further one hour. The reaction mixture was treated and then subjected to silica gel thin layer chromatography in a similar manner as in Example 2 to give 26.4 mg (46%) of Compound 4 (resinous).

IR (KBr) νmax(cm$^{-1}$): 2930, 2850, 1725, 1605, 1570, 1540, 1450, 1380, 1320, 1270, 1235, 1205, 1160, 1120, 1100, 1075, 1050, 1035, 995, 960, 920, 835, 780, 760, 725, 680, 650.

$^1$H-NMR (100MHz, CDCl$_3$) δ (ppm): 14.43(2H, s), 6.61(2H, s), 4.60–5.00(2H, m), 4.28(6H, s), 4.05(6H, s), 3.50(2H, dd, J=3, 13Hz), 2.93(2H, dd, J=10, 13Hz), 1.10(6H, d, J=7Hz), 0.50–1.50(26H, m).

EXAMPLE 6

Preparation of 14,17-di-O-decanoyl UCN-1028D (Compound 5)

UCN-1028D (38.6 mg) was allowed to react with 132 μl of decanoyl chloride (44 μl portions were added at one-hour intervals) in 1.5 ml of dichloromethane and 0.2 ml of pyridine with stirring under ice cooling for 4 hours. The reaction mixture was treated and then subjected to silica gel thin layer chromatography in a similar manner as in Example 2 to give 54.6 mg (91%) of Compound 5 (resinous).

IR (KBr) νmax(cm$^{-1}$): 2930, 2850, 1730, 1605, 1540, 1460, 1380, 1325, 1270, 1205, 1160, 1120, 1100, 1080, 1050, 1040, 995, 960, 835, 800, 780, 760, 720, 675, 650.

$^1$H-NMR (100MHz, CDCl$_3$) δ (ppm): 14.41(2H, s), 6.60(2H, s), 4.60–5.00(2H, m), 4.26(6H, s), 4.04(6H, s), 3.51(2H, dd, J=3, 13Hz), 2.94(2H, dd, J=10, 13Hz), 1.10(6H, d, J=7Hz), 0.50–1.80(38H, m).

EXAMPLE 7

Preparation of 14,17-di-O-dodecanoyl UCN-1028D (Compound 6)

UCN-1028D (42.1 mg) was subjected to reaction with dodecanoyl chloride in 1.5 ml of dichloromethane and 0.2 ml of pyridine with stirring under ice cooling for one hour. For the reaction, dodecanoyl chloride was added in 53 μl portions at the start and after 30 minutes. The reaction mixture was treated and then subjected to silica gel thin layer chromatography in a similar manner as in Example 2 to give 20.7 mg (30%) of Compound 6 (resinous).

IR (KBr) νmax(cm$^{-1}$): 2930, 2850, 1725, 1605, 1540, 1455, 1375, 1320, 1270, 1205, 1160, 1120, 1080, 1050, 1040, 995, 960, 920, 835.

$^1$H-NMR (100MHz, CDCl$_3$) δ (ppm): 14.37(2H, s), 6.59 (2H, s), 4.60–5.00(2H, m), 4.26(6H, s), 4.03(6H, s), 3.52(2H, dd, J=3, 13Hz), 2.93(2H, dd, J=10, 13Hz), 1.09(6H, d, J=7Hz), 0.50–1.60(46H, m).

EXAMPLE 8

Preparation of 14,17-di-O-pentenoyl UCN-1028D (Compound 7)

In 4 ml of dichloromethane was dissolved 101.4 mg of UCN-1028D, and 10 mg of 4-dimethylaminopyridine (hereinafter referred to as DMAP) was added to the solution. With stirring at room temperature, 56 μl of 4-pentenoic acid and 114 mg of dicyclohexylcarbodiimide (hereinafter referred to as DCC) were added to the mixture 3 times at one-hour intervals. The reaction was carried out for 6 hours. After 70 ml of ethyl acetate was added to the reaction mixture, precipitates were separated by filtration and washed with 30 ml of ethyl acetate. The washing and the filtrate were combined, and the organic layer was washed successively with 50 ml each of water (twice), 1 M hydrochloric acid, water, a saturated aqueous solution of sodium hydrogencarbonate (twice) and water (twice), dried over anhydrous sodium sulfate and concentrated under reduced pressure. The residue was dissolved in a small quantity of dichloromethane and the solution was loaded on a silica gel thin layer chromatography plate having a thickness of 2 mm (20 cm×20 cm) and developed with chloroform-methanol (100 : 2). The part of the silica gel on which a band of the main product was formed was scraped out and extracted with ethyl acetate. The extract was concentrated to give 119.4 mg (91%) of Compound 7.

Melting point: 112°–115° C.

IR (KBr) νmax (cm$^{-1}$): 3290, 3080, 2980, 2930, 2850, 1730, 1635, 1605, 1540, 1450, 1270, 1205, 1155, 1120, 1100, 1075, 1055, 980, 960, 920, 830, 780, 680.

$^1$H-NMR (100MHz, CDCl$_3$) δ (ppm): 14.48(2H, s), 6.40 (2H, s), 5.60–6.10(2H, m), 5.10–5.50(2H, m), 4.50–5.20(4H, m), 4.28(6H, s), 4.04(6H, s), 3.52 (2H, dd, J=3, 13Hz), 2.96(2H, dd, J=10, 13Hz), 1.12(6H, d, J=7Hz), 1.20–1.60(8H, m).

EXAMPLE 9

Preparation of 14,17-di-O-cyclohexanecarbonyl UCN-1028D (Compound 8)

UCN-1028D (37.0 mg) was allowed to react with 120 μl of cyclohexanecarbonyl chloride (30 μl portions were added at 30-minute intervals) in 2.0 ml of dichloromethane and 0.2 ml of pyridine under ice cooling for 2 hours. The reaction mixture was treated and then subjected to silica gel thin layer chromatography in a similar manner as in Example 2 to give 19.5 mg (38%) of Compound 8.

Melting point: 190°–193° C.

IR (KBr) νmax (cm$^{-1}$): 2970, 2930, 2850, 1720, 1605, 1540, 1450, 1390, 1380, 1310, 1270, 1245, 1205, 1155, 1120, 1100, 1075, 1055, 1035, 995, 965, 920, 830, 755, 675, 650.

$^1$H-NMR (100MHz, CDCl$_3$) δ (ppm): 14.53(2H, s), 6.60(2H, s), 4.70–5.10(2H, m), 4.26(6H, s), 4.02(6H, s), 3.48(2H, dd, J=3, 13Hz), 2.92(2H, dd, J=10, 13Hz), 1.13(6H, d, J=7Hz), 0.10–1.50(22H, m).

EXAMPLE 10

Preparation of 14,17-bis-O-phenylacetyl UCN-1028D (Compound 9)

UCN-1028D (37.5 mg) was allowed to react with 108 μl of phenylacetyl chloride (27 μl portions were added at one-hour intervals) in 1.5 ml of dichloromethane and 0.2 ml of pyridine at room temperature for 3.5 hours. The reaction mixture was treated and then subjected to silica gel thin layer chromatography in a similar manner as in Example 2 to give 44.8 mg (84%) of Compound 9.

Melting point: 75°–80° C.

IR (KBr) νmax (cm$^{-1}$): 3090, 3060, 3030, 2970, 2930, 2870, 2850, 1730, 1605, 1570, 1540, 1500, 1455, 1360, 1325, 1265, 1205, 1155, 1120, 1075, 1050, 1035, 990, 960, 915, 835, 760, 720, 705, 695, 680, 655.

$^1$H-NMR (100MHz, CDCl$_3$) δ (ppm): 14.42(2H, s), 6.60–7.50(10H, m), 6.57(2H, s), 4.60–5.00(2H, m), 4.23(6H, s), 3.92(6H, s), 3.54(2H, dd, J=3, 13Hz), 2.95(2H, dd, J=10, 13Hz), 2.19(4H, ABq), 1.07 (6H, d, J=7Hz).

EXAMPLE 11

Preparation of 14,17-bis-O-3-phenylpropionyl UCN-1028D (Compound 10)

UCN-1028D (35.1 mg) was allowed to react with 84 μl of 3-phenylpropionyl chloride (28 μl portions were added at 30-minute intervals) in 1.5 ml of dichloromethane and 0.2 ml of pyridine under ice cooling for one hour and 40 minutes. The reaction mixture was treated and then subjected to silica gel thin layer chromatography in a similar manner as in Example 2 to give 50.0 mg (96%) of Compound 10.

Melting point: 55°–58° C.

IR (KBr) νmax (cm$^{-1}$): 2970, 2930, 2850, 1730, 1605, 1540, 1455, 1380, 1325, 1275, 1210, 1160, 1120, 1080, 1055, 1040, 995, 965, 920, 835, 750, 700, 675.

$^1$H-NMR (100MHz, CDCl$_3$) δ (ppm): 14.46(2H, s), 6.60–7.50(10H, m), 6.27(2H, s), 4.70–5.10(2H, m), 4.30(6H, s), 3.60(6H, s), 3.54(2H, dd, J=3, 13Hz), 2.99(2H, dd, J=10, 13Hz), 1.14(6H, d, J=7Hz), 1.10–2.10(8H, m).

EXAMPLE 12

Preparation of 14,17-bis-O-4-phenylbutyryl UCN-1028D (Compound 11)

UCN-1028D (38.1 mg) was dissolved in 1.5 ml of dichloromethane and 0.2 ml of pyridine, and 4 mg of DMAP was added to the solution. With stirring at room temperature, 34 mg of 4-phenylbutyric acid and 43 mg of DCC were added to the mixture. After one hour, 34 mg of 4-phenylbutyric acid and 43 mg of DCC were added thereto, and after 2.5 hours, 24 mg of 4-phenylbutyric acid and 34 mg of DCC were added. The reaction was continued for further one hour. The reaction mixture was treated and then subjected to silica gel thin layer chromatography in a similar manner as in Example 8 to give 27.4 mg (47%) of Compound 11.

Melting point: 35°–38° C.

IR (KBr) νmax (cm$^{-1}$): 3110, 3090, 3070, 3030, 2940, 2860, 1730, 1605, 1540, 1455, 1380, 1330, 1270, 1205, 1160, 1140, 1120, 1080, 1050, 1035, 990, 960, 920, 835, 740, 700.

$^1$H-NMR (100MHz, CDCl$_3$) δ (ppm): 14.49(2H, s), 6.80–7.50(10H, m), 6.58(2H, s), 4.60–5.00(2H, m), 4.29(6H, s), 3.95(6H, s), 3.52(2H, dd, J=3, 13Hz), 2.95(2H, dd, J=10, 13H), 2.00(4H, t, J=7Hz), 1.10(6H, d, J=7Hz), 0.70–2.00(10H, m).

EXAMPLE 13

Preparation of 14,17-bis-O-1-naphthylacetyl UCN-1028D (Compound 12)

UCN-1028D (46.0 mg) was dissolved in 1.5 ml of dichloromethane and 0.2 ml of pyridine, and 4 mg of DMAP was added to the solution. The mixture was allowed to react with 94 mg of 1-naphthylacetic acid and 112 mg of DCC (a half of the amounts was added first, and after one hour, the remaining half was added) with stirring at room temperature for 2 hours. The reaction mixture was treated and then subjected to silica gel thin layer chromatography in a similar manner as in Example 8 to give 68.8 mg (93%) of Compound 12.

Melting point: 100°–104° C.

IR (KBr) νmax (cm$^{-1}$): 3050, 3000, 2980, 2940, 2850, 1730, 1600, 1565, 1540, 1510, 1450, 1400, 1360, 1320, 1270, 1205, 1160, 1120, 1075, 1050, 1035, 990, 960, 920, 835, 780, 760, 725, 675, 655.

$^1$H-NMR (100MHz, CDCl$_3$) δ (ppm): 14.47(2H, s), 7.10–8.00(14H, m), 6.60(2H, s), 4.70–5.10(2H, m), 4.25(6H, s), 3.80(6H, s), 3.57(2H, dd, J=3, 13Hz), 3.02(2H, dd, J=10, 13Hz), 2.67(4H, ABq), 1.08(6H, d, J=7Hz).

EXAMPLE 14

Preparation of 14,17-bis-O-phenyloxyacetyl UCN-1028D (Compound 13)

UCN-1028D (52.5 mg) was allowed to react with 78 μl of phenyloxyacetyl chloride (a 39 μl portion was added first and then 13 μl portions were added at 30-minute intervals) in 1.5 ml of dichloromethane and 0.2 ml of pyridine under ice cooling for 3 hours. The reaction mixture was treated and then subjected to silica gel thin layer chromatography in a similar manner as in Example 2 to give 77.5 mg (99%) of Compound 13.

Melting point: 71°–74° C.

IR (KBr) νmax (cm$^{-1}$): 3070, 2980, 2940, 2850, 1755, 1600, 1570, 1540, 1495, 1460, 1440, 1380, 1335, 1270, 1210, 1160, 1120, 1085, 1075, 1050, 1035, 990, 960, 920, 880, 835, 780, 755, 725, 690, 650.

$^1$H-NMR (100MHz, CDCl$_3$) δ (ppm): 14.40(2H, s), 6.70–7.50(10H, m), 6.44(2H, s), 4.70–5.10(2H, m), 4.35(6H, s), 3.70(6H, s), 3.59(2H, dd, J=3, 13Hz), 3.10(4H, ABq), 2.99(2H, dd, J=10, 13Hz), 1.17(6H, d, J=7Hz).

EXAMPLE 15

Preparation of 14,17-di-O-L-leucyl UCN-1028D bistrifluoroacetate (Compound 14)

In 1.0 ml of dichloromethane was dissolved 20.1 mg of UCN-1028D, and 2 mg of DMAP was added to the solution. With stirring at room temperature, 0.25 ml of a solution of t-butoxycarbonyl-L-leucine in dichloromethane prepared by dissolving 126 mg of t-butoxycarbonyl-L-leucine monohydrate in 1 ml of dichloromethane and drying the solution over molecular sieves 3A and 30 mg of DCC were added 3 times at 2-hour intervals. The reaction was continued for further one hour. The reaction mixture was treated and then subjected to silica gel thin layer chromatography in a similar manner as in Example 8 to give 35.8 mg (97%) of 14,17-bis-O-t-butoxycarbonyl-L-leucyl UCN-1028D.

$^1$H-NMR (100MHz, CDCl$_3$) δ (ppm): 14.53(2H, s), 6.59(2H, s), 4.60–5.00(2H, m), 4.24(6H, s), 4.04(6H, s), 2.90–3.90(8H, m), 1.33(18H, s), 1.03(6H, d, J=7Hz), 1.00–1.60(6H, m), 0.61(6H, d, J=6Hz), 0.54 (6H, d, J=6Hz).

The obtained 14,17-bis-O-t-butoxycarbonyl-L-leucyl UCN-1028D was allowed to react with 0.2 ml of trifluoroacetic acid in the presence of 0.02 ml of anisole by allowing the mixture to stand under ice cooling for one hour with occasional shaking. The reaction mixture was washed twice with 20 ml of hexane and once with 20 ml of diethyl ether. The residue was dissolved in methanol and concentrated to dryness under reduced pressure to give 33.1 mg (93%) of Compound 14 as bistrifluoroacetate.

Melting point: 127°–131° C.

IR (KBr) νmax (cm$^{-1}$): 2970, 2940, 2880, 1745, 1675, 1600, 1540, 1460, 1450, 1280, 1250, 1200, 1160, 1135, 1050, 1040, 990, 965, 920, 840, 800, 720.

$^1$H-NMR [100MHz, CDCl$_3$-CD$_3$OD (10:1)]δ (ppm): 6.65(2H, s), 4.60–5.00(2H, m), 4.24(6H, s), 4.10(6H, s), 3.67(2H, dd, J=3, 13Hz), 3.13(2H, dd, J=10, 13Hz), 2.76(2H, t, J=7Hz), 1.00–1.60(6H, m), 0.96(6H, d, J=7Hz), 0.60(12H, d, J=6Hz).

EXAMPLE 16

Preparation of 14,17-di-O-L-isoleucyl UCN-1028D bistrifluoroacetate (Compound 15)

In 1.0 ml of dichloromethane was dissolved 29.6 mg of UCN-1028D, and 0.2 ml of pyridine and 2 mg of DMAP were added to the solution. With stirring at room temperature, 48 mg of t-butoxycarbonyl-L-isoleucine and 44 mg of DCC were added 3 times at 1.5-hour intervals, and after further one hour, 16 mg of t-butoxycarbonyl-L-isoleucine and 14.5 mg of DCC were added. The reaction was continued for further one hour. The reaction mixture was treated and then subjected to silica gel thin layer chromatography in a similar manner as in Example 8 to give 33.2 mg (61%) of 14,17-bis-O-t-butoxycarbonyl-L-isoleucyl UCN-1028D.

$^1$H-NMR (100MHz, CDCl$_3$) δ (ppm): 14.52(2H, s), 6.60(2H, s), 4.50–4.90(2H, m), 4.26(6H, s), 4.08(6H, s), 3.57(2H, dd, J=3, 13Hz), 2.90–3.30(4H, m), 1.35 (18H, s), 1.08(6H, d, J=7Hz), 0.40–1.60(12H, m), 0.33(6H, d, J=6Hz).

The obtained 14,17-bis-O-t-butoxycarbonyl-L-isoleucyl UCN-1028D was treated with trifluoroacetic acid in the presence of anisole and subjected to the subsequent treatment in a similar manner as in Example 15 to give 26.3 mg (77%) of Compound 15 as bistrifluoroacetate.

Melting point: 145°–150° C.

IR (KBr) νmax (cm$^{-1}$): 2970, 2940, 2880, 1740, 1680, 1605, 1540, 1460, 1340, 1275, 1200, 1160, 1135, 1050, 990, 965, 920, 840, 800, 720.

$^1$H-NMR [100MHz, CDCl$_3$-CD$_3$OD (10 :1)]δ (ppm): 6.67(2H, s), 4.60–5.00(2H, m), 4.25(6H, s), 4.11(6H, s), 3.63(2H, dd, J=3, 13Hz), 3.11(2H, dd, J=10, 13Hz), 2.55(2H, d, J=4Hz), 1.06(6H, d, J=7Hz), 0.40–1.60 (18H, m).

EXAMPLE 17

Preparation of 14,17-di-O-D-phenylglycyl UCN-1028D bistrifluoroacetate (Compound 16)

In 1.5 ml of dichloromethane was dissolved 37.0 mg of UCN-1028D, and 0.2 ml of pyridine and 4 mg of DMAP were added to the solution. With stirring at room temperature, 53 mg of t-butoxycarbonyl-D-phenylglycine and 46 mg of DCC were added 4 times at one-hour intervals, and after further 1.5 hours, 29 mg of t-butoxycarbonyl-D-phenylglycine and 23 mg of DCC were added. The reaction was continued for further one hour. The reaction mixture was treated and then subjected to silica gel thin layer chromatography in a similar manner as in Example 8 to give 54.0 mg (79%) of 14,17-bis-O-t-butoxycarbonyl-D-phenylglycyl UCN-1028D.

$^1$H-NMR (100MHz, CDCl$_3$) δ (ppm): 14.39(2H, s), 6.40–7.30(10H, m), 6.58(2H, s), 5.00–5.30(2H, m), 4.70–5.10(2H, m), 4.33(2H, d, J=6Hz), 4.14(6H, s), 4.06(6H, s), 3.33(2H, dd, J=3, 13Hz), 2.91(2H, dd, J=10, 13Hz), 1.28(18H, s), 1.08(6H, d, J=7Hz).

The obtained 14,17-bis-O-t-butoxycarbonyl-D-phenylglycyl UCN-1028D was treated with trifluoroacetic acid in the presence of anisole and subjected to the subsequent treatment in a similar manner as in Example 15 to give 45.2 mg (84%) of Compound 16 as bistrifluoroacetate.

Melting point: 159°–162° C.

IR (KBr) νmax (cm$^{-1}$): 2980, 2940, 2850, 2650, 1740, 1675, 1605, 1560, 1540, 1460, 1450, 1380, 1320, 1280, 1235, 1200, 1180, 1160, 1135, 1050, 990, 960, 920, 835, 800, 720, 700.

$^1$H-NMR [100MHz, CDCl$_3$-CD$_3$OD (10 : 1)] δ (ppm): 6.50–7.50(10H, m), 6.58(2H, s), 4.80–5.20(2H, m), 4 21(6H, s), 4.08(6H, s), 3.20–3.60(4H, m), 2.84 (2H, dd, J=10, 13Hz), 1.15(6H, d, J=7Hz).

EXAMPLE 18

Preparation of 14,17-di-O-L-phenylalanyl UCN-1028D bistrifluoroacetate (Compound 17)

In 1.5 ml of dichloromethane was dissolved 28.5 mg of UCN-1028D, and 0.2 ml of pyridine and 3 mg of DMAP were added to the solution. With stirring at room temperature, 45 mg of t-butoxycarbonyl-L-phenylalanine and 36 mg of DCC were added 3 times at 1.5-hour intervals. The reaction was continued for further one hour. The reaction mixture was treated and then subjected to silica gel thin layer chromatography in a similar manner as in Example 8 to give 47.5 mg (88%) of 14,17-bis-O-t-butoxycarbonyl-L-phenylalanyl UCN-1028D.

$^1$H-NMR (100MHz, CDCl$_3$) δ (ppm): 14.57(2H, s), 6.60–7.40(10H, m), 6.42(2H, s), 4.60–5.10(2H, m), 4.30 (6H, s), 3.73(6H, s), 3.55(2H, dd, J=3, 13Hz), 3.28(2H, q, J=7Hz), 3.03(2H, dd, J=10, 13Hz), 1.30–2.20(4H, m), 1.28(18H, s), 1.03(6H, d, J=7Hz).

The obtained 14,17-bis-O-t-butoxycarbonyl-L-phenylalanyl UCN-1028D was treated with trifluoroacetic acid in the presence of anisole and subjected to the subsequent treatment in a similar manner as in Example 15 to give 35.6 mg (76%) of Compound 17 as bistrifluoroacetate.

Melting point: 147°–149° C.

IR (KBr) νmax (cm$^{-1}$): 3090, 3060, 2980, 2940, 2850, 2650, 1745, 1675, 1605, 1540, 1460, 1280, 1205, 1160, 1135, 1055, 990, 965, 915, 835, 800, 745, 720, 700.

$^1$H-NMR [100MHz, CDCl$_3$-CD$_3$OD (10:1)] δ (ppm): 6.70–7.40(10H, m), 6.57(2H, s), 4.60–5.10(2H, m), 4.22 (6H, s), 3.95(6H, s), 3.60(2H, dd, J=3, 13Hz), 2.90–3.30(4H, m), 2.42(4H, d, J=7Hz), 0.83(6H, d, J=7Hz).

EXAMPLE 19

Preparation of 14,17-di-O-D-phenylalanyl UCN-1028D bistrifluoroacetate (Compound 18)

In 2.0 ml of dichloromethane was dissolved 34.4 mg of UCN-1028D, and 3 mg of DMAP was added to the solution. With stirring at room temperature, 50 mg of t-butoxycarbonyl-D-phenylalanine and 38 mg of DCC were added 3 times at one-hour intervals. The reaction was continued for further one hour. The reaction mixture was treated and then subjected to silica gel thin layer chromatography in a similar manner as in Example 8 to give 14,17-bis-O-t-butoxycarbonyl-D-phenylalanyl UCN-1028D almost quantitatively.

$^1$H-NMR (100MHz, CDCl$_3$) δ (ppm): 14.66(2H, s), 6.20–7.30(10H, m), 6.10(2H, s), 4.90–5.30(2H, m), 4.38 (6H, s), 3.68(2H, dd, J=3, 13Hz), 3.42(6H, s), 3.00–3.30(4H, m), 1.24(18H, s), 1.00–1.40(10H, m).

The obtained 14,17-bis-O-t-butoxycarbonyl-D-phenylalanyl UCN-1028D was treated with trifluoroacetic acid in the presence of anisole and subjected to the subsequent treatment in a similar manner as in Example 15 to give 56.5 mg (87% based on UCN-1028D) of Compound 18 as bistrifluoroacetate.

Melting point: 185°–188° C.

IR (KBr) νmax (cm$^{-1}$): 3450, 3230, 2950, 2880, 2850, 2650, 1740, 1685, 1605, 1525, 1450, 1420, 1280, 1230, 1200, 1160, 1135, 1055, 990, 965, 920, 840, 825, 800, 745, 720, 700, 670.

$^1$H-NMR [100MHz, CDCl$_3$-CD$_3$OD (10:1)] δ (ppm): 6.10–7.30(10H, m), 6.03(2H, s), 4.90–5.30(2H, m), 4.38(6H, s), 3.64(2H, dd, J=3, 13Hz), 3.51(6H, s), 3.00–3.40(4H, m), 1.30(6H, d, J=7Hz), 1.20–1.40 (4H, m).

EXAMPLE 20

Preparation of 14,17-bis-O-N-methyl-L-phenylalanyl UCN-1028D bistrifluoroacetate (Compound 19)

In 2.0 ml of dichloromethane was dissolved 25.3 mg of UCN-1028D, and 3 mg of DMAP was added to the solution. With stirring at room temperature, 39 mg of t-butoxycarbonyl-N-methyl-L-phenylalanine and 30 mg of DCC were added 3 times at one-hour intervals. The reaction was continued for further one hour. The reaction mixture was treated and then subjected to silica gel thin layer chromatography in a similar manner as in Example 8 to give 48.0 mg (97%) of 14,17-bis-O-t-butoxycarbonyl-N-methyl-L-phenylalanyl UCN-1028D.

$^1$H-NMR [100MHz, CDCl$_3$-CD$_3$OD (10:1)] δ (ppm): 6.60–7.40(10H, m), 6.42(2H, s), 4.80–5.30(2H, m), 4.33 (6H, s), 3.77(6H, s), 3.59(2H, dd, J=3, 13Hz), 2.90–3.50(4H, m), 1.93(6H, s), 1.00–1.50(28H, m).

The obtained 14,17-bis-O-t-butoxycarbonyl-N-methyl-L-phenylalanyl UCN-1028D was treated with trifluoroacetic acid in the presence of anisole and subjected to the subsequent treatment in a similar manner as in Example 15 to give 28.2 mg (57%) of Compound 19 as bistrifluoroacetate.

Melting point: 105°–108° C.

IR (KBr) νmax (cm$^{-1}$): 3450, 2930, 2850, 1940, 1675, 1600, 1540, 1460, 1275, 1200, 1160, 1130, 1050, 990, 960, 920, 835, 795, 720, 700.

$^1$H-NMR [100MHz, CDCl$_3$-CD$_3$OD (10:1)] δ (ppm): 6.60–7.50(10H, m), 6.73(2H, s), 4.70–5.10(2H, m), 4.27 (6H, s), 4.10(6H, s), 3.65(2H, dd, J=3, 13Hz), 2.10–3.00(8H, m), 1.74(6H, s), 0.81(6H, d, J=7Hz).

EXAMPLE 21

Preparation of 14,17-di-O-L-prolyl UCN-1028D bistrifluoroacetate (Compound 20)

In 1.5 ml of dichloromethane was dissolved 33.0 mg of UCN-1028D, and 3 mg of DMAP was added to the solution. With stirring at room temperature, 39 mg of t-butoxycarbonyl-L-proline and 40 mg of DCC were added 4 times at one-hour intervals. The reaction was continued for further one hour. The reaction mixture was treated and then subjected to silica gel thin layer chromatography in a similar manner as in Example 8 to give 40.2 mg (71%) of 14,17-bis-O-t-butoxycarbonyl-L-prolyl UCN-1028D.

$^1$H-NMR (100MHz, CDCl$_3$) δ (ppm): 14.48(2H, s), 6.61(2H, s), 4.50–5.20(2H, m), 4.30(6H, s), 4.05(6H, s), 3.50(2H, dd, J=3, 13Hz), 2.98(2H, dd, J=10, 13Hz), 2.50–3.00(2H, m), 1.90–2.50(2H, m), 1.00–1.60 (32H, m).

The obtained 14,17-bis-O-t-butoxycarbonyl-L-prolyl UCN-1028D was treated with trifluoroacetic acid in the presence of anisole and subjected to the subsequent treatment in a similar manner as in Example 15 to give 38.2 mg (96%) of Compound 20 as bistrifluoroacetate.

Melting point: 102°–105° C.

IR (KBr) νmax (cm$^{-1}$): 3490, 2990, 2950, 2850, 2750, 1740, 1670, 1600, 1540, 1460, 1270, 1200, 1160, 1130, 1050, 990, 960, 915, 835, 795, 720.

$^1$H-NMR [100MHz, CDCl$_3$-CD$_3$OD (10:1)] δ (ppm): 6.69(2H, s), 4.50–5.20(2H, m), 4.25(6H, s), 4.12(6H, s), 3.90–4.20(2H, m), 3.65(2H, dd, J=3, 13Hz), 2.70–3.50(6H, m), 1.10–2.00(8H, m), 0.97(6H, d, J=7Hz).

EXAMPLE 22

Preparation of 14,17-bis-O-6-aminohexanoyl UCN-1028D bis-trifluoroacetate (Compound 21)

In 1.0 ml of dichloromethane was dissolved 29.8 mg of UCN-1028D, and 3 mg of DMAP was added to the solution. With stirring at room temperature, 38 mg of t-butoxycarbonyl-6-aminohexanoic acid and 37 mg of DCC were added 3 times at one-hour intervals. The reaction was continued for further one hour. The reaction mixture was treated and then subjected to silica gel thin layer chromatography in a similar manner as in Example 8 to give 27.8 mg (51%) of 14,17-bis-O-t-butoxycarbonyl-6-aminohexanoyl UCN-1028D.

$^1$H-NMR (100MHz, CDCl$_3$) δ (ppm): 14.40(2H, s), 6.63(2H, s), 4.60–5.00(2H, m), 4.26(6H, s), 4.06(6H, s), 3.49(2H, dd, J=3, 13Hz), 2.70–3.20(6H, m), 1.46 (18H, s), 1.09(6H, d, J=7Hz), 0.60–1.60(16H, m).

The obtained 14,17-bis-O-t-butoxycarbonyl-6-aminohexanoyl UCN-1028D was treated with trifluoroacetic acid in the presence of anisole and subjected to the subsequent treatment in a similar manner as in Example 15 to give 20.8 mg (76%) of Compound 21 as bistrifluoroacetate (resinous).

IR (KBr) νmax (cm$^{-1}$): 2940, 2880, 2860, 1725, 1680, 1605, 1530(br), 1455, 1275, 1250, 1200, 1180, 1160, 1130, 1050, 990, 965, 920, 835, 800, 720.

$^1$H-NMR [100MHz, CDCl$_3$-CD$_3$OD (10:1)] δ (ppm): 6.65(2H, s), 4.60–5.00(2H, m), 4.24(6H, s), 4.08(6H, s), 3.53(2H, dd, J=3, 13Hz), 2.95(2H, dd, J=10, 13Hz), 2.50–2.90(4H, m), 1.09(6H, d, J=7Hz), 0.60–1.60 (16H, m).

EXAMPLE 23

Preparation of 14,17-di-O-succinyl UCN-1028D (Compound 22)

In 2.0 ml of dichloromethane was dissolved 41.3 mg of UCN-1028D, and 0.5 ml of pyridine and 4 mg of DMAP were added to the solution. Then, 45 mg of succinic anhydride was added to the mixture δ times within 48 hours at room temperature. The reaction was carried out for 72 hours. After 30 ml of ethyl acetate was added to the reaction mixture, the organic layer was washed successively with 15 ml each of water (3 times), 1 M hydrochloric acid and water (3 times). The organic layer was then dried over anhydrous sodium sulfate and concentrated under reduced pressure. The residue was loaded on a silica gel thin layer chromatography plate having a thickness of 0.5 mm (20 cm×20 cm) and developed with chloroform-methanol (100:5). The part of the silica gel on which a band of the main product was formed was scraped out and extracted with methanol. After concentration, the residue was extracted with chloroform and the extract was concentrated to give 23.0 mg (41%) of Compound 22.

Melting point: 79°–82° C.

IR (KBr) νmax (cm$^{-1}$): 3450(br), 3100, 2990, 2940, 2850, 2650(br), 1730, 1710, 1600, 1540, 1450, 1270, 1210, 1160, 1050, 990, 960, 915, 830, 675.

$^1$H-NMR (100MHz, CDCl$_3$) δ (ppm): 14.30–14.40(2H, br), 8.80–9.60(2H, br), 6.59(2H, s), 4.60–5.00(2H, m), 4.24(6H, s), 4.00(6H, s), 3.51(2H, dd, J=3, 13Hz), 2.95(2H, dd, J=10, 13Hz), 0.70–1.80(8H, m).

EXAMPLE 24

Preparation of 14,17-bis-O-5-acetylthiopentanoyl UCN-1028D (Compound 23)

In 2.0 ml of dichloromethane was dissolved 74.5 mg of UCN-1028D, and 7 mg of DMAP was added to the solution. With stirring at room temperature, 77 mg of 5-acetylthiopentanoic acid and 84 mg of DCC were added 3 times at 30-minute intervals. The reaction was continued for further 30 minutes. The reaction mixture was treated and then subjected to silica gel thin layer chromatography in a similar manner as in Example 8 to give 103.0 mg (85%) of Compound 23 (resinous).

IR (KBr) νmax (cm$^{-1}$): 3350, 3100, 2940, 2850, 1730, 1690, 1605, 1570, 1540, 1460, 1360, 1270, 1210, 1160, 1130, 1120, 1075, 1050, 1040, 990, 960, 920, 835, 680, 620.

$^1$H-NMR (100MHz, CDCl$_3$) δ (ppm): 14.38(2H, s), 6.68(2H, s), 4.60–5.10(2H, m), 4.41(6H, s), 4.12(6H, s), 3.54(2H, dd, J=3, 13Hz), 2.94(2H, dd, J=10, 13Hz), 2.53(4H, t, J=6Hz), 2.32(6H, s), 1.50–1.90(4H, m), 1.10(6H, d, J=7Hz), 0.60–1.40(8H, m).

EXAMPLE 25

Preparation of 14,17-bis-O-p-acetoxybenzoyl UCN-1028D (Compound 24)

In 3.0 ml of dichloromethane was dissolved 110.8 mg of UCN-1028D, and 0.4 ml of pyridine was added to the solution. With stirring under ice cooling, 200 mg of p-acetoxybenzoyl chloride was added to the mixture in small portions. The reaction was carried out for 2 hours. The reaction mixture was treated and then subjected to silica gel thin layer chromatography in a similar manner as in Example 2 to give 56.0 mg (28%) of Compound 24.

Melting point: 123°–125° C.

IR (KBr) νmax (cm$^{-1}$): 3120, 3090, 2980, 2940, 2850, 1760, 1715, 1605, 1540, 1500, 1450, 1415, 1365, 1270, 1205, 1190, 1155, 1110, 1100, 1050, 1040, 1015, 995, 965, 915, 835, 760, 675.

$^1$H-NMR (100MHz, CDCl$_3$) δ (ppm): 14.52(2H, s), 6.40–7.20(8H, m), 6.33(2H, s), 4.80–5.30(2H, m), 4.35 (6H, s), 3.85(6H, s), 3.70(2H, dd, J=3, 13Hz), 3.20(2H, dd, J=10, 13Hz), 2.30(6H, s), 1.31(6H, d, J=7Hz).

EXAMPLE 26

Preparation of 14,17-bis-O-p-cyanobenzoyl UCN-1028D (Compound 25)

UCN-1028D (51.1 mg) was dissolved in 1.5 ml of dichloromethane and 0.2 ml of pyridine. The solution was subjected to reaction with 96 mg of p-cyanobenzoyl chloride (a half of the amount was added first, and after one hour, the remaining half was added) with stirring under ice cooling for 2 hours. The reaction mixture was treated and then subjected to silica gel thin layer chromatography in a similar manner as in Example 2 to give 55.3 mg (74%) of Compound 25.

Melting point: 121°–125° C.

IR (KBr) νmax (cm$^{-1}$): 3100, 2980, 2940, 2850, 2230, 1720, 1600, 1570, 1540, 1455, 1440, 1405, 1380, 1350, 1270, 1210, 1160, 1100, 1070, 1050, 1030, 1015, 990, 960, 915, 860, 835, 760, 720, 685.

$^1$H-NMR (100MHz, CDCl$_3$) δ (ppm): 14.48(2H, s), 6.80–7.30(8H, m), 6.40(2H, s), 5.00–5.40(2H, m), 4.36 (6H, s), 3.95(6H, s), 3.68(2H, dd, J=3, 13Hz), 3.15(2H, dd, J=10, 13Hz), 1.34(6H, d, J=7Hz).

EXAMPLE 27

Preparation of 14,17-bis-O-p-hydroxybenzoyl UCN-1028D (Compound 26)

In 1 ml of methanol was suspended 32.7 mg of Compound 24 obtained in Example 25, and 8.5 mg of sodium carbonate and 0.1 ml of water were added to the suspension. The mixture was stirred at room temperature for 25 minutes. About 30 ml of ethyl acetate was added to the reaction mixture and then 1 ml of 0.2 M hydrochloric acid was added thereto. After shaking, the ethyl acetate layer was washed 3 times with 30 ml of water, dried over anhydrous sodium sulfate and concentrated under reduced pressure. The residue was loaded on a silica gel thin layer chromatography plate having a thickness of 0.5 mm (20 cm×20 cm) and developed with chloroform-methanol (100 : 5). The part of the silica gel on which a band of the main product was formed was scraped out and extracted with methanol. The extract was concentrated and the residue was extracted with ethyl acetate. The extract was again concentrated to give 24.5 mg (83%) of Compound 26.

Melting point: 160°-165° C.

IR (KBr) $\nu$max (cm$^{-1}$): 3350(br), 2980, 2940, 2850, 1700, 1605, 1515, 1450, 1350, 1260, 1235, 1210, 1160, 1100, 1070, 1050, 1030, 990, 965, 915, 850, 830, 765, 740, 695, 680, 615.

$^1$H-NMR (100MHz, CDCl$_3$) $\delta$ (ppm): 14.55(2H, s), 7.80-8.60(2H, br), 6.20-6.90(8H, m), 6.15(2H, s), 4.80-5.20(2H, m), 4.34(6H, s), 3.84(6H, s), 3.70 (2H, dd, J=3, 13Hz), 3.16(2H, dd, J=10, 13Hz), 1.30(6H, d, J=7Hz).

EXAMPLE 28

Preparation of 14,17-bis-O-p-methoxybenzoyl UCN-1028D (Compound 27)

UCN-1028D (46.5 mg) was dissolved in 1.5 ml of dichloromethane and 0.2 ml of pyridine. With stirring under ice cooling, 86 mg of p-methoxybenzoyl chloride was added to the solution (a half of the amount was added first and after 30 minutes, the remaining half was added) and after one hour, 15 mg of p-methoxybenzoyl chloride was further added. The reaction was continued for further one hour. The reaction mixture was treated and then subjected to silica gel thin layer chromatography in a similar manner as in Example 2 to give 27.6 mg (40%) of Compound 27.

Melting point: 97°-100° C.

IR (KBr) $\nu$max (cm$^{-1}$): 3080, 2980, 2940, 2850, 1705, 1600, 1535, 1510, 1460, 1440, 1420, 1380, 1350, 1320, 1270, 1260, 1210, 1165, 1100, 1075, 1055, 1030, 995, 965, 920, 845, 835, 765, 720, 695, 675.

$^1$H-NMR (100MHz, CDCl$_3$) $\delta$ (ppm): 14.63(2H, s), 6.30-6.90(8H, m), 6.19(2H, s), 4.80-5.20(2H, m), 4.34 (6H, s), 3.81(6H, s), 3.79(6H, s), 3.65(2H, dd, J=3, 13Hz), 3.10(2H, dd, J=10, 13Hz), 1.29(6H, d, J=7Hz).

EXAMPLE 29

Preparation of 14,17-bis-O-p-methoxycarbonylbenzoyl UCN-1028D (Compound 28)

UCN-1028D (56.0 mg) was dissolved in 1.5 ml of dichloromethane and 0.2 ml of pyridine, and 60 mg of monomethyl terephthaloyl chloride was added to the solution with stirring under ice cooling. Then, 80 mg of monomethyl terephthaloyl chloride was further added by adding 20 mg portions at one-hour intervals. After completion of the addition, the reaction was continued for 1.5 hours. The reaction mixture was treated and then subjected to silica gel thin layer chromatography in a similar manner as in Example 2 to give 29.0 mg (33%) of Compound 28.

Melting point: 100°-105° C.

IR (KBr) $\nu$max (cm$^{-1}$): 3080, 2950, 2850, 1720, 1605, 1570, 1540, 1505, 1460, 1440, 1405, 1380, 1265, 1210, 1160, 1115, 1100, 1075, 1050, 1040, 1015, 990, 960, 920, 870, 835, 820, 725, 675.

$^1$H-NMR (100MHz, CDCl$_3$) $\delta$ (ppm): 14.55(2H, s), 6.80-7.60(8H, m), 6.34(2H, s), 4.90-5.30(2H, m), 4.37 (6H, s), 3.95(6H, s), 3.91(6H, s), 3.69(2H, dd, J=3, 13Hz), 3.21(2H, dd, J=10, 13Hz), 1.37(6H, d, J=7Hz).

EXAMPLE 30

Preparation of 14,17-bis-O-p-methylbenzoyl UCN-1028D (Compound 29)

UCN-1028D (56.2 mg) was dissolved in 1.0 ml of dichloromethane and 0.2 ml of pyridine, and 81 $\mu$l of p-methylbenzoyl chloride was added to the solution with stirring under ice cooling. The reaction was carried out for 2.5 hours. The reaction mixture was treated and then subjected to silica gel thin layer chromatography in a similar manner as in Example 2 to give 76.6 mg (95%) of Compound 29.

Melting point: 203°-206° C.

IR (KBr) $\nu$max (cm$^{-1}$): 3090, 3070, 2980, 2940, 2850, 1715, 1605, 1570, 1540, 1510, 1450, 1405, 1380, 1340, 1270, 1210, 1175, 1160, 1100, 1075, 1060, 1035, 1020, 990, 965, 920, 830, 750, 690, 670.

$^1$H-NMR (100MHz, CDCl$_3$) $\delta$ (ppm): 14.50(2H, s), 6.75 (8H, s), 6.28(2H, s), 4.80-5.20(2H, m), 4.35(6H, s), 3.84(6H, s), 3.73(2H, dd, J=3, 13Hz), 3.21 (2H, dd, J=10, 13Hz), 2.28(6H, s), 1.34(6H, d, J=7Hz).

EXAMPLE 31

Preparation of 14,17-bis-O-p-nitrobenzoyl UCN-1028D (Compound 30)

UCN-1028D (56.0 mg) was dissolved in 1.5 ml of dichloromethane and 0.2 ml of pyridine, and 74 mg of p-nitrobenzoyl chloride was added to the solution with stirring under ice cooling. After 2 hours, 42 mg of p-nitrobenzoyl chloride was added, and the reaction was continued for further 2 hours. The reaction mixture was treated and then subjected to silica gel thin layer chromatography in a similar manner as in Example 2 to give 77.4 mg (91%) of Compound 30.

Melting point: 137°-140° C.

IR (KBr) $\nu$max (cm$^{-1}$): 3120, 3080, 2980, 2940, 2850, 1720, 1605, 1525, 1450, 1440, 1345, 1270, 1205, 1155, 1110, 1100, 1050, 1010, 990, 960, 915, 870, 835, 780, 760, 715, 675.

$^1$H-NMR (100MHz, CDCl$_3$) $\delta$ (ppm): 14.37(2H, s), 6.80-7.80(8H, m), 6.43(2H, s), 4.90-5.30(2H, m), 4.38 (6H, s), 3.93(6H, s), 3.71(2H, dd, J=3, 13Hz). 3.17(2H, dd, J=10, 13Hz), 1.38(6H, d, J=7Hz).

EXAMPLE 32

Preparation of 14,17-di-O-1-naphthoyl UCN-1028D (Compound 31)

In 1.5 ml of dichloromethane was dissolved 39.9 mg of UCN-1028D, and 4 mg of DMAP was added to the solution. With stirring at room temperature, 65 mg of 1-naphthoic acid and 77 mg of DCC were added to the mixture. After 2 hours, 45 mg of 1-naphthoic acid and 57 mg of DCC were added, and the reaction was continued for further 18 hours. The reaction mixture was treated and then subjected to silica gel thin layer chromatography in a similar manner as in Example 8 to give 30.8 mg (50%) of Compound 31.

Melting point: 124°-128° C.

IR (KBr) $\nu$max (cm$^{-1}$): 3120, 3090, 3050, 2980, 2940, 2850, 1705, 1600, 1570, 1560, 1540, 1505, 1395, 1360, 1340, 1320, 1270, 1235, 1205, 1195, 1155, 1140, 1110, 1070, 1050, 1040, 990, 975, 960, 915, 865, 835, 810, 780, 720, 675, 650.

¹H-NMR (100MHz, CDCl₃) δ (ppm): 14.52(2H, s), 6.80–8.40(14H, m), 5.94(2H, s), 5.00–5.40(2H, m), 4.37 (6H, s), 3.77(2H, dd, J=3, 13Hz), 3.49(6H, s), 3.27(2H, dd, J=10, 13Hz), 1.37(6H, d, J=7Hz).

EXAMPLE 33

Preparation of 14,17-di-O-2-naphthoyl UCN-1028D (Compound 32)

UCN-1028D (40.7 mg) was dissolved in 1.5 ml of dichloromethane and 0.2 ml of pyridine, and 4 mg of DMAP was added to the solution. With stirring at room temperature, 64 mg of 2-naphthoic acid and 80 mg of DCC were added to the mixture. After 1.5 hours, 64 mg of 2-naphthoic acid and 80 mg of DCC were added, and the reaction was continued for further 5 hours. The reaction mixture was treated and then subjected to silica gel thin layer chromatography in a similar manner as in Example 8 to give 39.0 mg (61%) of Compound 33.

Melting point: 132°–135° C.

IR (KBr) νmax (cm⁻¹): 3060, 2940, 2850, 1710, 1605, 1540, 1450, 1355, 1275, 1230, 1210, 1195, 1155, 1140, 1120, 1090, 1050, 995, 965, 955, 920, 865, 835, 775, 760.

¹H-NMR (100MHz, CDCl₃) δ (ppm): 14.60(2H, s), 7.30–7.90(12H, m), 6.80–7.00(2H, m), 5.49(2H, s), 5.00–5.40(2H, m), 4.41(6H, s), 3.80(2H, dd, J=3, 13Hz), 3.24(2H, dd, J=10, 13Hz), 3.13(6H, s), 1.38(6H, d, J=7Hz).

EXAMPLE 34

Preparation of 14,17-di-O-isonicotinyl UCN-1028D (Compound 33)

In 2.0 ml of dichloromethane was dissolved 45.8 mg of UCN-1028D, and 4 mg of DMAP was added to the solution. With stirring at room temperature, 31 mg of isonicotinic acid and 52 mg of DCC were added to the mixture 3 times at one-hour intervals, and the reaction was continued for further 3 hours. After about 30 ml of ethyl acetate was added to the reaction mixture, precipitates were separated by filtration and washed with 10 ml of ethyl acetate. The ethyl acetate layer was washed 3 times with 15 ml each of water, dried over anhydrous sodium sulfate and concentrated under reduced pressure. The residue was loaded on a silica gel thin layer chromatography plate having a thickness of 0.5 mm (20 cm×20 cm) and developed with chloroform-methanol (100 : 5). The part of the silica gel on which a band of the main product was formed was scraped out and extracted with methanol. After concentration, the residue was extracted with dichloromethane and the extract was concentrated to give 38.8 mg (61%) of Compound 33.

Melting point: 240° C. or above.

IR (KBr) νmax (cm⁻¹): 3000, 2980, 2940, 2850, 1725, 1605, 1530, 1460, 1405, 1275, 1205, 1155, 1105, 1050, 990, 965, 915, 830, 750, 700.

¹H-NMR (100MHz, CDCl₃) δ (ppm): 14.55(2H, s), 8.22(4H, d, J=6Hz), 6.62(4H, d, J=6Hz), 6.37(2H, s), 5.00–5.40(2H, m), 4.40(6H, s), 3.87(6H, s), 3.68(2H, dd, J=3, 12Hz), 3.12(2H, dd, J=10, 12Hz), 1.33 (6H, d, J=7Hz).

EXAMPLE 35

Preparation of 14,17-bis-O-pyrazine-2-carbonyl UCN-1028D (Compound 34)

In 2.0 ml of dichloromethane was dissolved 41.4 mg of UCN-1028D, and 4 mg of DMAP was added to the solution. With stirring at room temperature, 28 mg of pyrazine-2-carboxylic acid and 47 mg of DCC were added to the mixture 3 times at 1.5-hour intervals. The reaction was continued for further 2 hours. The reaction mixture was treated and purified by silica gel thin layer chromatography in a similar manner as in Example 34 to give 44.3 mg (77%) of Compound 34.

Melting point: 240° C. or above

IR (KBr) νmax (cm⁻¹): 3080, 3050, 3000, 2980, 2940, 2850, 1750, 1605, 1535, 1450, 1350, 1270, 1205, 1150, 1120, 1055, 1015, 985, 960, 915, 830, 770.

¹H-NMR (100MHz, CDCl₃) δ (ppm): 14.38(2H, s), 8.43 (2H, d, J=2Hz), 8.24(2H, d, J=2Hz), 7.97(2H, s), 6.28(2H, s), 5.00–5.40(2H, m), 4.35(6H, s), 3.88 (6H, s), 3.68(2H, dd, J=3, 13Hz), 3.20(2H, dd, J=10, 13Hz), 1.33(6H, d, J=7Hz).

EXAMPLE 36

Preparation of 14,17-di-O-2-furoyl UCN-1028D (Compound 35)

UCN-1028D (41.7 mg) was dissolved in 2.0 ml of dichloromethane and 0.2 ml of pyridine. With stirring at room temperature, 22 μl of 2-furoyl chloride was added to the solution 4 times at one-hour intervals, and the reaction was continued for further one hour. The reaction mixture was treated and purified by silica gel thin layer chromatography in a similar manner as in Example 2 to give 35.1 mg (63%) of Compound 35.

Melting point: 240° C. or above.

IR (KBr) νmax (cm⁻¹): 3140, 2980, 2930, 2850, 1720, 1605, 1565, 1540, 1470, 1390, 1340, 1280, 1205, 1180, 1155, 1105, 1070, 1050, 985, 960, 935, 910, 880, 825, 760, 680.

¹H-NMR (100MHz, CDCl₃) δ (ppm): 14.49(2H, s), 7.11(2H, s), 6.42(2H, s), 5.98(2H, d, J=4Hz), 5.75(2H, d, J=4Hz), 4.80–5.20(2H, m), 4.31(6H, s), 3.91(6H, s), 3.62(2H, dd, J=3, 13Hz), 3.11(2H, dd, J=10, 13Hz), 1.05(6H, d, J=7Hz).

EXAMPLE 37

Preparation of 14,17-bis-O-methoxycarbonyl UCN-1028D (Compound 36)

UCN-1028D (34.3 mg) was dissolved in 2.0 ml of dichloromethane and 0.2 ml of pyridine. With stirring under ice cooling, 15 μl of methyl chloroformate was added to the solution 4 times at 30-minute intervals, and the reaction was continued for further 30 minutes. The reaction mixture was treated and purified by silica gel thin layer chromatography in a similar manner as in Example 2 to give 32.1 mg (81%) of Compound 36.

Melting point: 177°–179° C.

IR (KBr) νmax (cm⁻¹): 3000, 2980, 2950, 2850, 1740, 1605, 1540, 1440, 1265, 1205, 1155, 1120, 1070, 990, 965, 940, 910, 845, 830, 780, 760, 740.

¹H-NMR (100MHz, CDCl₃) δ (ppm): 14.45(2H, s), 6.60(2H, s), 4.40–4.80(2H, m), 4.25(6H, s), 4.05(6H, s), 3.56(2H, dd, J=3, 12Hz), 3.00(2H, dd, J=10, 12Hz), 2.92(6H, s), 1.08(6H, d, J=7Hz).

EXAMPLE 38

Preparation of 14,17-bis-O-benzyloxycarbonyl UCN-1028D (Compound 37)

UCN-1028D (54.3 mg) was dissolved in 2.0 ml of dichloromethane and 0.2 ml of pyridine. With stirring under ice cooling, 88 μl of benzyl chloroformate was added to the solution 4 times at one-hour intervals, and the reaction was continued for further one hour. The reaction mixture was treated and purified by silica gel thin layer chromatography in a similar manner as in Example 2 to give 61.8 mg (76%) of Compound 37.

Melting point: 76°–78° C.

IR (KBr) νmax (cm⁻¹): 3090, 3070, 3040, 2980, 2940, 2850, 1740, 1605, 1540, 1455, 1380, 1260, 1205, 1155, 1130, 1050, 990, 960, 915, 835, 780, 735, 695.

$^1$H-NMR (100MHz, CDCl$_3$) δ (ppm): 14.49(2H, s), 6.80–7.40(10H, m), 6.43(2H, s), 4.40–4.80(2H, m), 4.27 (6H, s), 4.30(4H, ABq), 3.78(6H, s), 3.58(2H, dd, J=3, 13Hz), 3.05(2H, dd, J=10, 13Hz), 1.08(6H, d, J=7Hz).

EXAMPLE 39

Preparation of 14,17-bis-O-phenyloxycarbonyl UCN-1028D (Compound 38)

UCN-1028D (54.3 mg) was dissolved in 2.0 ml of dichloromethane and 0.2 ml of pyridine. With stirring under ice cooling, 20 μl of phenyl chloroformate was added to the solution 3 times at 30-minute intervals, and after further minutes, 10 μl of phenyl chloroformate was added. The reaction was continued for further one hour. The reaction mixture was treated and purified by silica gel thin layer chromatography in a similar manner as in Example 2 to give 68.0 mg (87%) of Compound 38.

Melting point: 221°–224° C.

IR (KBr) νmax (cm⁻¹): 3000, 2970, 2930, 2850, 1750, 1605, 1520, 1490, 1455, 1420, 1340, 1255, 1210, 1155, 1115, 1105, 1075, 1055, 1025, 990, 965, 920, 770, 715, 695, 670, 650, 630.

$^1$H-NMR (100MHz, CDCl$_3$) δ (ppm): 14.48(2H, s), 6.40–7.60(10H, m), 6.34(2H, s), 4.60–5.00(2H, m), 4.28 (6H, s), 3.73(6H, s), 3.66(2H, dd, J=3, 13Hz), 3.12(2H, dd, J=10, 13Hz), 1.21(6H, d, J=7Hz).

EXAMPLE 40

Preparation of 14,17-bis-O-methanesulfonyl UCN-1028D (Compound 39)

UCN-1028D (30.9 mg) was dissolved in 2.0 ml of dichloromethane and 0.2 ml of pyridine. With stirring under ice cooling, 13 μl of methanesulfonyl chloride was added to the solution 4 times at 30-minute intervals, and the reaction was continued for further 4 hours. The reaction mixture was treated and purified by silica gel thin layer chromatography in a similar manner as in Example 2 to give 32.7 mg (83%) of Compound 39.

Melting point: 102°–105° C.

IR (KBr) νmax (cm⁻¹): 3050, 3030, 3020, 2980, 2940, 2850, 1605, 1540, 1455, 1350, 1335, 1275, 1210, 1175, 1160, 1050, 995, 965, 920, 895, 840, 785, 750.

$^1$H-NMR (100MHz, CDCl$_3$) δ (ppm): 14.49(2H, s), 6.60(2H, s), 4.30–4.70(2H, m), 4.30(6H, s), 4.60(6H, s), 3.52(2H, dd, J=3, 13Hz), 3.08(2H, dd, J=10, 13Hz), 1.80(6H, s), 1.31(6H, d, J=7Hz).

EXAMPLE 41

Preparation of 14,17-bis-O-p-toluenesulfonyl UCN-1028D (Compound 40)

UCN-1028D (52.3 mg) was dissolved in 2.0 ml of dichloromethane and 0.2 ml of pyridine. With stirring under ice cooling, 55 mg of p-toluenesulfonyl chloride was added to the solution 3 times at 2-hour intervals, and the reaction was continued for further 3 hours. The reaction mixture was treated and purified by silica gel thin layer chromatography in a similar manner as in Example 2 to give 65.4 mg (80%) of Compound 40.

Melting point: 168°–170° C.

IR (KBr) νmax (cm⁻¹): 3080, 3070, 3000, 2980, 2950, 2850, 1605, 1525, 1450, 1420, 1380, 1360, 1350, 1270, 1215, 1170, 1150, 1120, 1095, 1045, 985, 965, 915, 890, 815, 750, 660.

$^1$H-NMR (100MHz, CDCl$_3$) δ (ppm): 14.33(2H, s), 6.60–6.90(8H, m), 6.54(2H, s), 4.20–4.60(2H, m), 4.15 (12H, s), 3.34(2H, dd, J=3, 13Hz), 2.90(2H, dd, J=10, 13Hz), 2.29(6H, s), 1.36(6H, d, J=7Hz).

EXAMPLE 42

Preparation of 14,17-bis-O-propylaminocarbonyl UCN-1028D (Compound 41)

UCN-1028D (47.7 mg) was allowed to react with 0.1 ml of propyl isocyanate in 0.2 ml of chloroform at 55° C. The reaction was carried out for 20 hours by adding 0.1 ml of propyl isocyanate every 5 hours. The reaction mixture was loaded on a silica gel thin layer chromatography plate having a thickness of 2 mm (20 cm×20 cm) and developed with chloroform-methanol (100 : 2). The part of the silica gel on which a band of the main product was formed was scraped out and extracted with ethyl acetate. The extract was concentrated to give 31.7 mg (51%) of Compound 41.

Melting point: 240° C. or above.

IR (KBr) νmax (cm⁻¹): 3430, 3380, 2970, 2940, 2870, 1710, 1605, 1525, 1455, 1275, 1240, 1215, 1160, 1055, 990, 965, 920, 900, 830, 770, 730, 680, 660.

$^1$H-NMR (100MHz, CDCl$_3$) δ (ppm): 14.43(2H, s), 6.60(2H, s), 4.50–4.90(2H, m), 4.25(6H, s), 4.04(6H, s), 3.49(2H, dd, J=3, 13Hz), 2.90(2H, dd, J=10, 13Hz), 2.80–3.20(2H, m), 1.90–2.70(4H, m), 1.10(6H, d, J=7Hz), 0.70–1.10(4H, m), 0.55(6H, t, J=7Hz).

EXAMPLE 43

Preparation of 14,17-bis-O-phenylaminocarbonyl UCN-1028D (Compound 42)

In 0.2 ml of toluene was suspended 29.5 mg of UCN-1028D, and 18 μl of phenyl isocyanate was added to the suspension. The mixture was subjected to reaction at 70° C. for one hour. The reaction mixture was loaded on a silica gel thin layer chromatography plate having a thickness of 0.5 mm (20 cm×20 cm) and developed with chloroform-methanol (100 : 2). The part of the silica gel on which a band of the main product was formed was scraped out and extracted with ethyl acetate. The extract was concentrated to give 22.7 mg (54%) of Compound 42.

Melting point: 209°–212° C.

IR (KBr) νmax (cm⁻¹): 3410, 3330, 3130, 3070, 3030, 2990, 2930, 2830, 1730, 1605, 1540, 1520, 1450, 1280, 1215, 1200, 1160, 1055, 990, 965, 895, 835, 760, 740, 695.

$^1$H-NMR [100MHz, CDCl$_3$-CD$_3$OD (10 :1)] δ (ppm): 6.30–7.50(10H, m), 6.20(2H, s), 4.50–4.90(2H, m), 3.96 (6H, s), 3.65(2H, dd, J=3, 13Hz), 3.58(6H, s), 3.05(2H, dd, J=10, 13Hz), 2.80–3.20(2H, m), 1.20 (6H, d, J=7Hz).

EXAMPLE 44

Preparation of UCN-1028 iso-D (Compound 43)

In an atmosphere of argon, 1.004 g of UCN-1028D was heated under reflux in 200 ml of xylene for 2 hours. The reaction mixture was concentrated under reduced pressure. The residue was loaded on silica gel thin layer chromatography plates (3 sheets) having a thickness of 2 mm (20 cm ×20 cm) and developed with chloroform-methanol (10 : 1). The part of the silica gel on which a band of the main product below the band of UCN-1028D was formed was scraped out and extracted with ethyl acetate. The extract was concentrated to give 501 mg (49.9%) of Compound 43.

Melting point: 221°-224° C.

IR (KBr) νmax (cm⁻¹): 3430(br), 2970, 2930, 2850, 1605, 1525, 1450, 1405, 1340, 1270, 1230, 1215, 1155, 1105, 1075, 1040, 990, 980, 930, 835, 680, 650.

¹H-NMR [100MHz, CDCl₃-CD₃OD (10:1)] δ (ppm): 6.60(2H, s), 4.22(6H, s), 4.10(6H, s), 3.71(2H, dd, J=5, 13Hz), 3.55(2H, m), 2.94(2H, dd, J=8, 13Hz), 0.30(6H, d, J=7Hz).

EXAMPLE 45

Preparation of 14,17-di-O-benzoyl UCN-1028 iso-D (Compound 44)

In 2.0 ml of dichloromethane and 0.2 ml of pyridine was dissolved 19.6 mg of UCN-1028 iso-D obtained in Example 44. With stirring under ice cooling, 20 μl of benzoyl chloride was added to the solution, and after one hour, 20 μl of benzoyl chloride was further added. The reaction was continued for further 1.5 hours. The reaction mixture was treated and purified by silica gel thin layer chromatography in a similar manner as in Example 2 to give 24.1 mg (89%) of Compound 44.

Melting point: 105°-108° C.

IR (KBr) νmax (cm⁻¹): 2980, 2930, 2850, 1705, 1605, 1540, 1450, 1270, 1205, 1155, 1140, 1105, 1095, 1065, 1020, 990, 960, 910, 835, 705

¹H-NMR (100MHz, CDCl₃) δ (ppm): 14.40(2H, s), 7.10-7.70(10H, m), 6.35(2H, s), 4.90-5.30(2H, m), 4.32 (6H, s), 4.02(6H, s), 3.76(2H, dd, J=4, 13Hz), 3.50(2H, dd, J=10, 13Hz), 0.66(6H, d, J=7Hz).

What is claimed is:

1. A UCN-1028D derivative represented by the general formula:

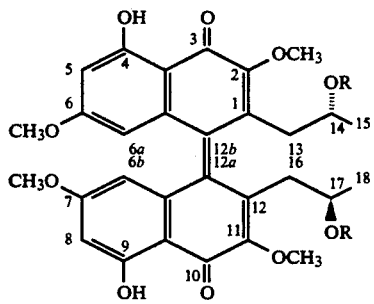

wherein R represents hydrogen, (a)

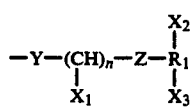

wherein Y represents

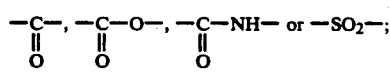

n represents an integer of 0 to 4; Z represents O, NH or a single bond; R₁ represents an aryl; X₁ represents hydrogen, OR₂ (wherein R₂ represents hydrogen, a straight-chain or branched alkyl group having 1 to 5 carbon atoms, or a straight-chain or branched alkanoyl group having 1 to 5 carbon atoms), NR₃R₄ (wherein R₃ and R₄ independently refer to R₂, and R₂ has the same significance as defined above), NO₂, SR₂ (wherein R₂ has the same significance as defined above) CN or CO₂R₅ (wherein R₅ represents hydrogen or an alkyl group having 1 to 5 carbon atoms), and when n is 2 or more, X₁ may be the same or different from each other; X₂ and X₃ each represents a substituent on R₁ and independently represent X₁ (wherein X₁ has the same significance as defined above) or a straight-chain or branched alkyl group having 1 to 5 carbon atoms; with the proviso that when n is 0, Z represents a single bond, and when n is 0, Y is

and R₁ is phenyl, the perylenequinone ring takes R configuration with respect to the bond between 6a and 6b, or (b) —Y—R₆ wherein Y has the same significance as defined above; and R₆ represents a straight-chain or branched alkyl group having 1 to 12 carbon atoms, a cyclic alkyl group having 3 to 8 carbon atoms, a straight-chain or branched alkenyl group having 2 to 6 carbon atoms and which contains 1 to 3 double bonds, or a group obtained by substituting at least one hydrogen of these groups with X₄ (wherein X₄ refers to X₁ excluding hydrogen, and X₁ has the same significance as defined above).

2. A compound according to claim 1, wherein R is hydrogen.

3. A compound according to claim 1, wherein R is

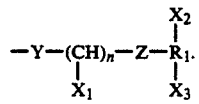

4. A compound according to claim 3, wherein Y is

n=0 and Z is a single bond.

5. A compound according to claim 4, wherein R₁ is phenyl and X₂ and X₃ independently represent hydrogen, methyl, hydroxyl, methoxy, acetoxy, methoxycarbonyl, cyano or nitro.

6. A compound according to claim 1, wherein R is —Y—R₆.

7. A compound according to claim 6, wherein Y is

and R₆ is a member selected from the group consisting of methyl, propyl, pentyl, hexyl, nonyl, undecyl and 3-butenyl.

8. A compound according to claim 1, wherein R is a member selected from the group consisting of L-leucyl, L-isoleucyl, D-phenylglycyl, L-phenylalanyl, D-phenylalanyl, N-methyl-L-phenylalanyl, L-prolyl and 6-aminohexanoyl.

9. A pharmaceutical composition comprising a pharmaceutical carrier and, as an active ingredient, an effective amount of the UCN-1028D derivative defined in claim 1.

* * * * *